United States Patent [19]

Kanngard et al.

[11] Patent Number: 5,672,384

[45] Date of Patent: Sep. 30, 1997

[54] METHOD OF ELIMINATING MOISTURE PROBLEMS IN HOUSING

[76] Inventors: Bengt Kanngard, Taljestensvagen 6 S-141, 34 Huddinge; Jan Kristensson, Pl. 10840 Gribby S-761, 72 Norrtalje, both of Sweden

[21] Appl. No.: 693,237
[22] PCT Filed: Feb. 8, 1995
[86] PCT No.: PCT/SE95/00123
  § 371 Date: Sep. 12, 1996
  § 102(e) Date: Sep. 12, 1996
[87] PCT Pub. No.: WO95/21801
  PCT Pub. Date: Aug. 17, 1995

[30] Foreign Application Priority Data

Feb. 10, 1994 [SE] Sweden .................................. 9400438

[51] Int. Cl.$^6$ ........................................................ B05D 7/22
[52] U.S. Cl. .................... 427/230; 427/299; 427/403; 427/407.1; 427/443.2
[58] Field of Search ............................... 427/230, 299, 427/403, 407.1, 443.2

*Primary Examiner*—Bernard Pianalto
*Attorney, Agent, or Firm*—Young & Thompson

[57] ABSTRACT

Method of eliminating moisture problems in housing and premises with supporting structures made of concrete, comprising hydrophobic impregnation of a supporting concrete construction/bedding with a hydrophobic agent with a molecular size such that the impregnation becomes open to diffusion, and thereafter application of acidic ion exchange particles dispersed in a carrier on the bedding for the formation of a layer.

9 Claims, No Drawings

METHOD OF ELIMINATING MOISTURE PROBLEMS IN HOUSING

The present invention relates to a method of eliminating moisture problems in housing and premises having a concrete supporting structure.

BACKGROUND

Most of the housing and premises in Sweden were built after 1945. Up to the industrialization of the erection during the seventies, comparatively few different building materials were used. The experience of these materials, such as stone, wood, bricks, concrete, sheet metal etc., based on few raw materials, was extensive. Concrete is a building material which has been used in constructions built in situ as well as in prefabricated constructions. Concrete as a building material is formed when cement, gravel, stone and water is mixed in order to obtain the desired properties. Nowadays concrete contains a large number of chemical substances among other things in order to obtain better characteristics in manufacture, transport and erection. Construction concrete for the supporting elements of the buildings such as the floor and the walls contains, among other things, Portland cement, the characteristics of which counteract damage of the reinforcement steel.

Flow putty is used to even out concrete floors before laying down the floor covering, such as linoleum, PVC carpets and different types of wooden floors. Flow putty is manufactured from cement, dried sand and different additives. The most common flow additive formerly was casein, which is a protein which was added to flow putty in order to enhance the flowing-out properties. Now other additives are used, e.g. melamine.

The cause of the problems which are summarized under the term "sick houses" can primarily be derived from the high moisture load, which e.g. the concrecte floors are subjected to during the building phase, as well as the acute moisture damages in the form of "water damages" which occur during the user phase of housing and premises. Nowadays it is known that high pH-values, e.g. an alcaline environment, creates a combination effect where for example PVC carpets and softeners therein as well as carpet adhesives, are broken down by alcaline moisture from the concrete as well as when ammonia escapes from flow putty.

It is not only the moisture in itself that is the problem but also the character of the moisture, i.e. its high pH-value, which is the reason for a large part of the sick-house-problems.

THE INVENTION

The object of the invention is to provide a method of substantially reducing the damages in view of health problems caused by the above mentioned technical deficiencies.

This is achieved with the method according to the present invention which is characterized by hydrophobic impregnation of the supporting concrete construction/bedding with the aid of a hydrophobic agent with a molecular size such that the impregnation becomes open to diffusion, and thereafter treatment of the bedding with an acid ionexchanger having been mixed into a carrier.

Thanks to the hydrophobic impregnation future water uptake by the concrete is reduced to a minimum while at the same time it is left to diffusion so that moisture is not confined therein. This is of utmost importance for a tile on the ground in which the relative humidity can be up to 100%.

Preferably, silanes and/or siloxanes are used, which have a suitable molecular size. The acidic ion exchanger then takes care of the alcalinity of the moisture coming from the alcaline Portland cement and possible ammonia being formed at the degradation of flow putty etc. This means that the esther hydrolysis reaction which breaks down softening agents in e.g. PVC carpets and adhesives for floor carpets, normally a phtalic acid esther such as di(2-ethyl hexyl)-phtalate, practically ceases. The pH of the moisture should be less than 9, and preferably be less than or equal to 8.

Hereby is achieved that, besides that the problems with sick houses are reduced or eliminated, the life of the floor carpets increases from one or a few years to at least 15 years. The normal time of use for PVC carpets in premises and housing are 8–10 years.

The choice of the ion exchange material is not critical but for the fact that it should be acidic for taking care of the $OH^-$ ions in the moisture. By using an ion exchanger with $H^+$ ions water is formed, which is preferred. Examples of useful ion exchange materials are zeolites, sulfonated carbon and synthetic ion exchange resins.

The particles of the ion exchange material should have a size within the interval 50–350 μm. The size of the particles within the interval is decided depending on the surface layer chosen. Examples of suitable particle sizes for different surface layers will be evident from the table below.

Advantageously, 10–15% ion exchange particles are added, depending on the particle size chosen and on the demands that are put on the new surface layer, see the table below, to a carrier consisting of e.g. a copolymer of acrylic acid esther and styrene, in order for the ion exchange process to proceed at least during 15 years of time, which exceeds the expected life of a PVC carpet which is 8–10 years. Further, a successive drying-out of the concrete occurs, wherefor the consumption diminishes. The amount and size of the particles is not decisive for the function of the invention, but these quantities are important for flowability and spreadability as well as the eveness of the bedding after covering. In comparison it could be mentioned that if the moisture problems should be eliminated without using the invention the concrete would have to be dried down to about 70% before application of a surface layer. The time required for this can be up to about 1 year for a normal concrete floor.

The method according to the invention thus comprises two steps and these are described below. 1. Hydrophobic Impregnation of the Bedding The object of the treatment is to protect concrete and flow putty, respectively, against future water absorption. The agent used shall thus penetrate into the mineral building material with low porosity, whereby the small molecules of the agent form a water repellant layer on the capillary walls, without the pores and capillaries, respectively, becoming obstructed. Thus, the construction shall be open to diffusion after performed treatment. When treating of very dry underlying floors of concrete and flow putty, the uptake of water diminishes from 25 ml/24 hours to about 0.35–1.0 ml/24 hours at e.g. inundation or water leakage, i.e. a 25 times enhancement compared to constructions not having been treated.

Hydrophobic impregnation pet se have been performed earlier on concrete constructions, but then silicon-based products dissolved in white spirit have been used. Hereby the concentration of active component is only about 25%. Already from environmental reasons this technique can not be used today. Further, the particles are large, in the order of magnitude μm and instead of penetration a tacky covering is obtained.

Epoxy based products, which according to known technique are applied in layers with 2–3 mm thickness, result in, among other things, that the underlying floor becomes diffusion tight. When having a tile on the ground, the concrete will have a constant high moisture content with a high pH-value and this moisture can act negatively on the epoxy layer, and does not give any long term solution to the problem of sick houses.

At hydrophobic impregnation of concrete according to the invention the impregnation agent consists of a 100% active component, such as Dynasalan® BHN, which is based on isobutyl triethoxy silane.

The molecules of this product have a dimension of about 1.85 nm (18.5 Ångströms), resulting in that it has a very high penetration capacity in composite material such as concrete and flow putty, respectively.

At impregnation of porous materials, such as light weight concrete, sand stone, advantageously a solution diluted with water is used, such as Dynasalan® BSM 2000, which is provided with a concentration of 20% active substance in water, and thus is also completely free of organic solvants.

The control of the quality of the impregnation can be performed with new methods. The impregnation agent can be mixed with a fluorescent substance, which in an alkylsilane based impregnation solution can be fluorescin [2(3, 6-di-hydroxyxantyl)-bensoic acid] or other substance with fluorescing characteristics and suitable solubility. After performed impregnation the depth of the impregnation is thereafter controlled with the aid of ultraviolet light. Previously known control methods such as e.g. the funnel method are limited in their use at e.g. laying of floor carpets in housing and premises. This control method can also be used on horizontal concrete constructions, such as the underside of bridges and their edge beams, which advantageously are impregnated in order to counteract water and salt uptake.

2. Treatment With Ion Exchangers

As mentioned above it is not the moisture in itself that causes the damages but instead the character of the moisture. Most of the supporting elements of buildings such as the floors consist of concrete wherein the cement paste is Portland cement. This type of cement has characteristics such as a high pH-value in order to limit corrosion damages of the reinforcement steel. In construction concrete with a normal moisture content the pH-value normally lies between 11.0 and 13. This environment, possibly in combination with the previously uses flow putty products create a flow of alcaline moisture towards carpet adhesive and PVC carpets, whereby different substances are released, such as 2-ethyl hexanol when the softening agent is di(2-ethylhexyl)-phtalate.

The other step of the method according to the invention comprises a surface treatment with ion exchanger having been mixed into, for example, acrylic dispersions such as carpet adhesive and/or primer. The particle size of the ion exchanger in this connection preferably lies between 50 and 150 µm and get a very effective binding against the underlying floor.

In summary, with the present invention is accomplished that
- the bedding is protected from water uptake at e.g. water damages since the treatment results in that only a week increace of the moisture content in e.g. concrete floors is obtained during long and lasting "inundations",
- the problems with the chemical degradation of the softening agents in PVC carpets are reduced or eliminated,
- a low moisture content and a low pH-value in the concrete bedding is guaranteed,
- a floor construction open to diffusion is guaranteed,
- a lasting concept for healthy and water-proof floors and a good indoor climate is created.

In the following table the presently preferred amounts of ion exchanger materials in % pro litre acrylic dispersion dependant on the bedding in question is given; the presently preferred particle size depending on the surface layer chosen; and finally a suitable amount of hydrophobic agent depending on the moisture content of the bedding.

| Consumption of material/m² for different types of subfloor | Dry ion exchange mass in %/liter acryl dispersion | | | |
|---|---|---|---|---|
| | 50 µm | 100 µm | 200 µm | 350 µm |
| Type of floor structure | | | | |
| Concrete floor, on the ground | 20 | 25 | 30 | 35 |
| Concrete floor, creep foundation | 20 | 25 | 30 | 35 |
| Concrete floor, intermediate | 10 | 10 | 20 | 25 |
| Floor with top floor of tree, e.g. parquetry | | | | |
| Floor with surface layer of linoleum or PVC carpets | | | | |
| Hydrophobution Alkylsilane type CIAB* on very dry subfloor (w = 3%) = about 1.0–1.2 liter/m² | | | | |
| Alkylsilane type CIAB* on moist subfloor (w = 5%) = about 0.6–0.7 liter/m² | | | | |

*Alkylsilane type CIAB = Dynasylan BHN + Fluorescing substance

We claim:

1. Method of eliminating moisture problems in housing and premises having supporting structures made of concrete, which comprises:
   hydrophobically impregnating a supporting concrete bedding with a hydrophobic agent having a molecular size such that the impregnation becomes open to diffusion, and
   thereafter applying on the bedding an acidic ion exchange material having particles dispersed in a carrier in order to form a layer on the bedding.

2. Method according to claim 1, wherein the hydrophobic impregnation is performed with at least one of silanes and siloxanes.

3. Method according to claim 1, wherein the hydrophobic impregnation is performed with isobutyl triethoxy silane.

4. Method according to claim 1, wherein the particles of the ion exchange material have a particle size within the interval of 50–350 µm.

5. Method according to claim 4, wherein the ion exchange particles are dispersed in an adhesive intended for gluing a surface layer.

6. Method according to claim 5, wherein the adhesive is a PVC carpet adhesive.

7. Method according to claim 4, wherein the ion exchange particles are dispersed in a primer and are applied on the bedding before applying a surface layer.

8. Method according to claim 4, wherein the ion exchange particles are dispersed in an acrylic dispersion.

9. Method according to claim 1, wherein the ion exchange material used is selected from the group consisting of zeolites, sulfonated carbon and synthetic ion exchange resins.

* * * * *